(12) United States Patent
Karlsson et al.

(10) Patent No.: US 8,377,969 B2
(45) Date of Patent: Feb. 19, 2013

(54) COMPOUNDS FOR USE IN THE TREATMENT OF CANCER

(75) Inventors: Jan Olof G. Karlsson, Trondheim (NO); Tino Kurz, Linköping (SE); Rolf Andersson, Vikingstad (SE)

(73) Assignee: PledPharma AB, Stockholm (SE)

( * ) Notice: Subject to any disclaimer, the term of this patent is extended or adjusted under 35 U.S.C. 154(b) by 223 days.

(21) Appl. No.: 12/808,144

(22) PCT Filed: Dec. 12, 2008

(86) PCT No.: PCT/SE2008/051450
§ 371 (c)(1),
(2), (4) Date: Aug. 5, 2010

(87) PCT Pub. No.: WO2009/078794
PCT Pub. Date: Jun. 25, 2009

(65) Prior Publication Data
US 2010/0298271 A1  Nov. 25, 2010

Related U.S. Application Data (60) Provisional application No. 61/006,010, filed on Dec. 14, 2007.

(51) Int. Cl.
A61K 31/444 (2006.01)
A61K 31/506 (2006.01)

(52) U.S. Cl. ........................ 514/335; 514/269
(58) Field of Classification Search .................. 514/335, 514/269
See application file for complete search history.

(56) References Cited

U.S. PATENT DOCUMENTS

| | | | |
|---|---|---|---|
| 6,147,094 A | 11/2000 | Towart et al. | |
| 6,258,828 B1 | 7/2001 | Towart et al. | |
| 6,310,051 B1 | 10/2001 | Karlsson et al. | |
| 6,391,895 B1 | 5/2002 | Towart et al. | |
| 7,351,722 B2 | 4/2008 | Batteux et al. | |
| 2004/0142907 A1 | 7/2004 | Batteux et al. | |
| 2007/0148154 A1 | 6/2007 | Weill et al. | |
| 2010/0298271 A1 | 11/2010 | Karlsson et al. | |

FOREIGN PATENT DOCUMENTS

| | | |
|---|---|---|
| EP | 0936915 B1 | 10/2002 |
| EP | 0910360 B1 | 11/2002 |
| EP | 1060174 B1 | 9/2004 |
| EP | 1054670 B1 | 3/2005 |
| EP | 1381364 B1 | 8/2006 |
| WO | 97/49409 A1 | 12/1997 |
| WO | 02/087579 A1 | 11/2002 |

OTHER PUBLICATIONS

International Search Report dated Feb. 23, 2009, for International Application No. PCT/SE2008/051450.
Written Opinion dated Feb. 23, 2009, for International Application No. PCT/SE2008/051450.
EMA: "Europaischer offentlicher Beurteilungbericht (EPAR) Teslascan" retrieved from the internet: URL:http://www.ema.europa.eu/docs/de_DE/document_library/EPAR_—_Summary_for_the_public/human/000137/WC500036330.pdf, Apr. 1, 2007.
Extended Search Report in EP Application No. 08863324.3 issued on Dec. 10, 2010. EP Application No. 08863324.3 is a foreign counterpart of U.S. Appl. No. 12/808,144.
Jerome Alexandre et al, Improvement of the Therapeutic Index of Anticancer Drugs by the Superoxide Dismutase Mimic Mangafodipir, Journal of the National Cancer Institute, vol. 98, No. 4, pp. 236-244, Feb. 15, 2006.
Sassia Bedda et al, Mangafodipir prevents liver injury induced by acetaminophen in the mouse, Journal of Hepatology, 39 (2003) pp. 765-772.
Heidi Burok et al, Manganese Dipyridoxyl Diphosphate: MRI Contrast Agent with Antioxidative and Cardioprotective Properties?, Biochemical and Biophysical Research Communications, 254:768-772 (1999).
Janelle Crossgrove et al, Manganese toxicity upon overexposure, NMR in Biomedicine (2004);17:544-553.
Valerie Cizewski Culotta et al, Activation of superoxide dismutases: Putting the metal to the pedal, NIH Public Access Author Manuscript, published as Biochim Biophys Acta. (2006) 1763(7): 747-758.
Salvatore Cuzzocrea et al, Antioxidant Therapy: A New Pharmacological Approach in Shock, Inflammation, and Ischemia/Reperfusion Injury, Pharmacol Rev 53:135-159,2001.
Doroshow, Redox Modulation of Chemotherapy-Induced Tumor Cell Killing and Normal Tissue Toxicity, Journal of the National Cancer Institute, vol. 98, No. 4, Feb. 15, 2006.

(Continued)

*Primary Examiner* — Charanjit Aulakh
(74) *Attorney, Agent, or Firm* — Porter Wright Morris & Arthur LLP (57) ABSTRACT

Compound of Formula I or a salt thereof for treating cancer, wherein X represents CH or N; $R^1$ represents hydrogen or —$CH_2COR^5$; $R^5$ represents hydroxy, optionally hydroxylated alkoxy, amino or alkylamido; $R^2$ represents $ZYR^6$; Z represents a bond, or a $C_{1-3}$ alkylene or oxoalkylene group optionally substituted by $R^7$; Y represents a bond, an oxygen atom or $NR^6$; $R^6$ is a hydrogen atom, $COOR^8$, an alkyl, alkenyl, cycloalkyl, aryl or aralkyl group optionally substituted by one or more selected from $COOR^8$, $CONR^8_2$, $NR^8_2$, $OR^8$, =$NR^8$, =O, $OP(O)(OR^8)R^7$ and $OSO_3M$; $R^7$ is hydroxy, an optionally hydroxylated, optionally alkoxylated alkyl or aminoalkyl group; $R^8$ is a hydrogen atom or an optionally hydroxylated, optionally alkoxylated alkyl group; M is a hydrogen atom or one equivalent of a physiologically tolerable cation; $R^3$ represents $C_{1-8}$ alkylene, 1,2-cykloalkylene, or 1,2-arylene, optionally substituted with $R^7$; and $R^4$ represents hydrogen or $C_{1-3}$ alkyl.

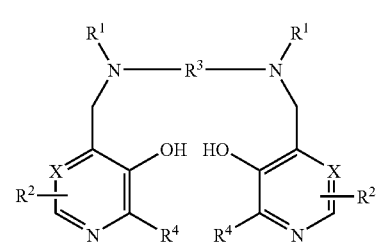

17 Claims, 7 Drawing Sheets

OTHER PUBLICATIONS

Marcella Folin et al, Zinc content of normal human serum and its correlation with some hematic parameters, BioMetals 1994, 7:75-79.

Irwin Fridovich, Oxygen Toxicity: A Radical Explanation, The Journal of Experimental Biology, 201:1203-1209 (1998).

Alan Hazell et al, Alzheimer type II astrocytic changes following sub-acute exposure to manganese and its prevention by antioxidant treatment, Neuroscience Letters, 396 (2006) 167-171.

Hustvedt et al, Plasma Pharmacokinetics, Tissue Distribution and Excretion of MnDPDP in the Rat and Dog After Intravenous Administration, Acta Radiologica, 38 (1997) 690-699.

Karlsson, Antioxidant activity of mangafodipir is not a new finding, Letters to the Editor / Journal of Hepatology, 40 (2004) 869-873.

Karlsson et al, Cardioprotective Effects of the MR Contrast Agent MnDPDP and its Metabolite MnPLED Upon Reperfusion of the Ischemic Porcine Myocardium, Acta Radiologica, 42 (2001) 540-547.

Karlsson et al, The Magnetic Resonance Imaging Contrast Agent Mangafodipir Exerts Antitumor Activity via a Previously Described Superoxide Dismutase Mimetic Activity, Cancer Res 2006; 66: (1). Jan. 1, 2006, p. 598.

King et al, Zinc Homeostasis in Humans1, The Journal of Nutrition (2000), pp. 1360s-1366s.

Laurent et al, Controlling Tumor Growth by Modulating Endogenous Production of Reactive Oxygen Species, Cancer Research, 2005; 65(3):948-956, Feb. 1, 2005.

Muscoli et al, On the selectivity of superoxide dismutase mimetics and its importance in pharmacological studies, British Journal of Pharmacology (2003) 140, 445-460.

Rocklage et al, Manganese(II) N,N'-Dipyridoxylethylenediamine-N,N'-diacetate 5,5'-Bis(phosphate). Synthesis and Characterization of a Paramagnetic Chelate for Magnetic Resonance Imaging Enhancement, Inorganic Chemistry, vol. 28, No. 3:477-485 (1989).

Scheuhammer et al, Influence of Chronic MnCl2 and EDTA Treatment on Tissue Levels and Urinary Excretion of Trace Metals in Rats, Arch. Environm. Contam. Toxicol., 11:515-520 (1982).

Schmidt et al, Stability and transmetallation of the magnetic resonance contrast agent MnDPDP measured by EPR, J Biol Inorg Chem (2002) 7: 241-248.

Skjold et al, Relaxation Enhancing Properties of MnDPDP in Human Myocardium, Journal of Magnetic Resonance Imaging, 20:948-952 (2004).

Southon et al, NMR Relaxation Studies With MnDPDP, Acta Radiologica, 38 (1997) 708-716.

Toft et al, Metabolism and Pharmacokinetics of MnDPDP in Man, Acta Radiologica 38 (1997) 677-689.

Wendland, Applications of manganese-enhanced magnetic resonance imaging (MEMRI) to imaging of the heart, NMR in Biomedicine, 2004;17:581-594.

Yokel, Brain Uptake, Retention, and Efflux of Aluminum and Manganese, Environmental Health Perspectives, vol. 110, Supplement 5, Oct. 2002, 699-704.

Yri et al, Mangafodipir as a cytoprotective adjunct to chemotherapy—a case report, Acta Oncologica, Jan. 2009, 1-3.

COMPOUNDS FOR USE IN THE TREATMENT OF CANCER

This application is a U.S. National Phase of International Application No. PCT/SE2008/051450, filed Dec. 12, 2008, designating the U.S. and published in English as WO 2009/078794 on Jun. 25, 2009 which claims the benefit of U.S. Provisional Patent Application No. 61/006,010 filed Dec. 14, 2007.

FIELD OF INVENTION

The present invention relates to a compound for use in the treatment of cancer. The invention also relates to the use of the compound in the manufacture of a medicament for the treatment of cancer. Also disclosed is a method of treatment of cancer in the human or non-human body wherein said method comprises administrating to said body a compound as mentioned above. The invention further relates to a pharmaceutical composition comprising the above mentioned compound and a compound having cyto-protective ability. The invention also relates to the use of the pharmaceutical composition in the manufacture of a medicament for treatment of cancer.

BACKGROUND

EP0910360, U.S. Pat. No. 6,147,094, EP0936915, U.S. Pat. No. 6,258,828, EP1054670, U.S. Pat. No. 6,310,051, EP1060174, U.S. Pat. No. 6,391,895 disclose the use of dipyridoxyl based chelating agents and their metal chelates and the use of certain manganese containing compounds, in particular manganese chelates, in medicine. The use of such compounds as cell protective agents in cancer therapy is also disclosed. The above cited documents disclose that certain chelating agents, in particular dipyridoxyl and aminopolycarboxylic acid based chelating agents, and their metal chelates are effective in treating or preventing anthracycline-induced cardiotoxicity, ischaemia-reperfusion-induced injuries and atherosclerosis. Dipyridoxyl based chelating agents and their chelates with trivalent metals have previously been described by Taiferro (Inorg. Chem. 1984; 23:1183-1192).

DPDP(N,N'-bis-(pyridoxal-5-phosphate)-ethylenediamine-N,N'-diacetic acid), and the dephosphorylated counterpart PLED (N,N'-dipyridoxyl ethylenediamine-N,N'-diacetic acid) are dipyridoxyl compounds able to chelate metals. It has previously been described that the manganese chelates of these compounds, MnDPDP and its dephosphorylated counterpart MnPLED, possess catalytic antioxidant activity, i.e., a superoxide dismutase (SOD) mimetic activity. These compounds have been shown to have a protective effect in normal cells e.g., against the cytostatic drug doxorubicin and ischemia-reperfusion. It is the SOD mimetic activity, which is an inherent property of redox-active manganese ($Mn^{2+}/Mn^{3+}$) bound to DPDP/PLED (Brurok et al., Biochem Biophys Res Commun. 1999; 254:768-721), that explains the protective effects. Consequently, Brurok and co-workers (1999) have shown that the PLED metal complex loses its catalytic activity after replacing redox-active manganese with redox-inactive zink ($Zn^{2+}$).

Laurent et al. (Cancer Res. 2005; 6:948-56) and Alexandre et al., (J Natl Cancer Inst. 2006; 98:236-44) have recently described that MnDPDP (equivalent to the ready-to-use MRI contrast agent Teslascan) not only increased survival of normal cells but also increased cancer cell death during cytostatic treatment, e.g., with oxaliplatin. Cytostatic drugs may cause cancer cell death by elevating intracellular $H_2O_2$ and inducing apoptosis. The Laurent et al., hypothesis was that MnDPDP due to its SOD mimetic activity elevated intracellular $H_2O_2$ and hence acted in synergy with cytostatic drugs. Since the basal level of $H_2O_2$ is much lower in normal cells compared to cancer cells, the authors suggested that elevation from a low $H_2O_2$ level induced cell survival in normal cells. They furthermore suggested that elevation from a much higher basal level of $H_2O_2$ in cancer cells at the same time resulted in apoptotic signalling and hence cell death. Consequently, these authors suggested that both these effects, i.e., the increase in cancer cell death and survival of normal cells, were caused by the SOD mimetic activity of MnDPDP, an activity which is absolutely dependent on redox-active manganese. It has also been shown that intravenous injection of both the mother compound MnDPDP and its metabolite MnPLED into mice gave rise to protection against certain cytostatic drugs (EP0910360 and U.S. Pat. No. 6,147,094).

When MnDPDP is intravenously injected into humans about 70% of the administered manganese is released. For diagnostic imaging use and for occasional therapeutic use, dissociation of manganese from MnDPDP represents no major problem. However, for more frequent use accumulated manganese toxicity may represent a serious toxicological problem, particularly when it comes to neurotoxicity (Crossgrove & Zheng; NMR Biomed. 2004; 17:544-53). Thus, for frequent therapeutic use, as in cancer treatment, compounds that dissociate manganese should be avoided.

A number of anti-tumour agents are associated with adverse side effects. Paclitaxel, for example, is one such cytostatic drug which has shown anti-neoplastic activity against a variety of malignant tissues, including those of the breast, However, at the dosages required to have an anti-neoplastic effect, paclitaxel has a number of adverse side-effects which include cardiovascular irregularities as well as haematological and gastrointestinal toxicity. Oxaliplatin, in particular in combination with 5-fluorouracil (5-FU), is another example of a cytostatic drug that is effective in the treatment of colorectal cancer but its use is restricted by severe adverse side-effects, in particular haematological toxicity and neurotoxicity. Severe side-effects also restrict the use of radiation therapy in cancer.

There is hence an unmet medical need to find new chemotherapeutic drugs with fewer side-effects, in addition to find methods to protect normal cells against injuries caused by cancer treatment.

DESCRIPTION OF THE INVENTION

The present invention provides a compound with cancer cell-killing ability for use in the treatment of cancer. The invention also provides the use of a compound of the invention in the manufacture of a medicament for treatment of cancer. The invention further comprises a method of treatment of cancer in the human or non-human body, wherein said method comprises administrating to said body a compound of the invention. Also disclosed is a pharmaceutical composition which comprises the above mentioned compound and a second compound having a cyto-protective ability, i.e. the ability to protect normal cells during cancer treatment from the side-effects caused by chemotherapeutic drugs and radiation. Also provided is the use of a pharmaceutical composition according to the invention in the manufacture of a medicament for treatment of cancer. The invention also relates to a method of treatment of cancer in the human or non-human body, wherein said method comprises administrating to said body the compound of the invention.

A first aspect of the invention is directed to a compound of Formula I

Formula I or a salt thereof, for use in the treatment of cancer, wherein
X represents CH or N,
each $R^1$ independently represents hydrogen or —$CH_2COR^5$;
$R^5$ represents hydroxy, optionally hydroxylated alkoxy, amino or alkylamido;
each $R^2$ independently represents a group $ZYR^6$; Z represents a bond, or a $C_{1-3}$ alkylene or oxoalkylene group optionally substituted by a group $R^7$;
Y represents a bond, an oxygen atom or a group $NR^6$;
$R^6$ is a hydrogen atom, a group $COOR^8$, an alkyl, alkenyl, cycloalkyl, aryl or aralkyl group optionally substituted by one or more groups selected from $COOR^8$, $CONR^8_2$, $NR^8_2$, $OR^8$, =$NR^8$, =O, $OP(O)(OR^8)R^7$ and $OSO_3M$;
$R^7$ is hydroxy, an optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation; e.g. an alkali or alkaline earth cation, an ammonium ion or an organic amine cation, such as meglumine ion;
$R^3$ represents a $C_{1-8}$ alkylene group, preferably a $C_{1-6}$, e.g. a $C_{2-4}$, alkylene group, a 1,2-cykloalkylene group, or a 1,2-arylene group, optionally substituted with $R^7$; and each $R^4$ independently represents hydrogen or $C_{1-3}$ alkyl and wherein the compound is optionally a chelate with one or two $Na^+$ or $K^+$, but a combination of one $Na^+$ and one $K^+$ is also possible.

In an embodiment of the invention $R^5$ is hydroxy, $C_{1-8}$ alkoxy, ethylene glycol, glycerol, amino or $C_{1-8}$ alkylamido;
Z is a bond or a group selected from $CH_2$, $(CH_2)_2$, CO, $CH_2CO$, $CH_2CH_2CO$ or $CH_2COCH_2$; Y is a bond;
$R^8$ is a mono- or poly(hydroxy or alkoxylated) alkyl group or a group of the formula $OP(O)(OR^8)R^7$; and $R^7$ is hydroxy, or an unsubstituted alkyl or aminoalkyl group.

In another embodiment of the invention $R^3$ is ethylene and each group $R^1$ represents —$CH_2COR^5$ in which $R^5$ is hydroxy.

In yet another embodiment of the invention the compound of Formula I is N,N'-dipyridoxyl ethylenediamine-N,N'-diacetic acid (PLED).

In a further embodiment of the invention the compound of Formula I is N,N'-bis-(pyridoxal-5-phosphate)-ethylenediamine-N,N'-diacetic acid (DPDP).

In another embodiment of the invention is described the use of a compound of Formula I, as defined above, in the manufacture of a medicament for treatment of cancer. The cancer may be any type of cancer e.g. leukaemia, breast cancer, colorectal cancer, liver cancer and metastases thereof. The medicament may comprise pharmaceutically acceptable carriers or excipients.

A second aspect of the invention is directed to a method of treatment of cancer in the human or non-human body, said method comprising administrating to said body a compound of Formula I according to the invention.

A third aspect of the invention is directed to a pharmaceutical composition comprising a first compound of Formula I, as defined hereinabove, and a second compound having a cyto-protective ability.

In another embodiment of the invention the second compound comprised in the pharmaceutical composition is a metal chelate comprising a compound of Formula I as defined above.

In yet another embodiment of the invention the metal chelate comprised in the pharmaceutical composition has a $K_a$ value preferably in the range of from $10^8$ to $10^{24}$, more preferably in a range of from $10^{10}$ to $10^{22}$ and most preferably in the range of from $10^{12}$ to $10^{20}$.

In a yet further embodiment of the invention the metal chelate comprised in the pharmaceutical composition has a lower $K_a$ value than the $K_a$ value of an iron ($Fe^{3+}$) chelate comprising a compound of Formula I as defined above, by a factor of at least $10^3$.

In still another embodiment of the invention the metal in the metal chelate comprised in the pharmaceutical composition is manganese ($Mn^{2+}$ or $Mn^{3+}$) or copper ($Cu^+$ or $Cu^{2+}$).

In another embodiment of the invention the first compound of the pharmaceutical composition is N,N'-dipyridoxyl ethylenediamine-N,N'-diacetic acid and the second compound is a metal chelate comprising N,N'-dipyridoxyl ethylenediamine-N,N'-diacetic acid. The metal in the metal chelate is preferably manganese or copper.

In a preferred embodiment of the invention the first compound of the pharmaceutical composition is N,N'-bis-(pyridoxal-5-phosphate)-ethylenediamine-N,N'-diacetic acid and the second compound is a metal chelate comprising N,N'-dipyridoxyl ethylenediamine-N,N'-diacetic acid. The metal in the metal chelate is preferably manganese or copper.

In a further embodiment of the invention the second compound of the pharmaceutical composition according to the invention may preferably constitute $1/100$ to $99/100$ of the first compound, at a molar basis.

In a yet further embodiment of the invention is provided the pharmaceutical composition according to the invention for use in the treatment of cancer.

In a fourth aspect of the invention is provided a kit comprising a preparation of a first active ingredient, which is a compound of Formula I as defined above, a preparation of a second active ingredient, which is a metal chelate comprising a compound of Formula I as defined above, and optionally instructions for the simultaneous, sequential or separate administration of the preparations to a patient in need thereof.

In a fifth aspect of the invention is provided the use of a pharmaceutical composition according to the invention in the manufacture of a medicament for treatment of cancer. The cancer may be any type of cancer e.g. leukaemia, breast cancer, colon cancer, liver cancer and metastases thereof.

In another embodiment of the invention is provided the use of a pharmaceutical composition according to the invention, wherein the medicament further comprises pharmaceutically acceptable carriers or excipients.

In a sixth aspect of the invention is provided a method of treatment of cancer in a patient in need of such treatment, comprising the step of administrating to said patient a cancer inhibiting amount of a pharmaceutical composition according to the invention, optionally in combination with pharmaceutically acceptable carriers and excipients.

In a further embodiment of the invention is provided a method wherein the pharmaceutical composition is administered together with one or more other anti-cancer drug(s). The anti-cancer drug could be any anticancer drug, e.g., doxorubicin, epirubicin, oxaliplatin, cisplatin, carboplatin, paclitaxel, 5-fluorouracil, cyclophosphamide, gemcitabine, irinotecan, and methotrexate.

In another embodiment of the invention is provided a method, wherein the pharmaceutical composition as described above and the one or more other anti-cancer drug(s) are administered simultaneously, separately or sequentially to said patient.

In a further embodiment of the invention is provided a method of treatment as described above, wherein the treatment is combined with radiation therapy.

The invention should also be understood to include the use of the pharmaceutical composition according to the invention in the manufacture of a medicament for treatment of cancer The compounds of Formula I as defined above for use in the invention should be understood to be therapeutically active and physiologically preferred compounds.

As used herein the terms "alkyl" and "alkylene" include straight-chained and branched, saturated and unsaturated hydrocarbons. The term "1,2-cykloalkylene" includes both cis and trans cycloalkylene groups and alkyl substituted cycloalkylene groups having from 5-8 carbon atoms. The term "1,2-arylene" includes phenyl and naphthyl groups and alkyl substituted derivatives thereof having from 6 to 10 carbon atoms.

Unless otherwise specified, any alkyl, alkylene or alkenyl moiety may conveniently contain from 1 to 20, preferably 1-8, more preferably 1-6 and especially preferably 1-4 carbon atoms.

Cycloalkyl, aryl and aralkyl moieties may conveniently contain 3-18, preferably 5-12 and especially preferably 5-8 ring atoms. Aryl moieties comprising phenyl or naphthyl groups are preferred. As aralkyl groups, phenyl $C_{1-8}$ alkyl, especially benzyl, are preferred.

Where groups may optionally be substituted by hydroxyl groups, this may be monosubstitution or polysubstituition and, in the case of polysubstitution, alkoxy and/or hydroxyl substituents may be carried by alkoxy substitutents.

In Formula I, $R^5$ is preferably hydroxyl, $C_{1-8}$ alkoxy, ethylene glycol, glycerol, amino or $C_{1-8}$ alkylamido. Preferably each group $R^1$ represents —$CH_2COR^5$ in which $R^5$ is hydroxy.

In the compound of Formula I, Z is preferably a bond or a group selected from $CH_2$, $(CH_2)_2$, CO, $CH_2CO$, $CH_2CH_2CO$ or $CH_2COCH_2$. Preferably, Y represents a bond.

The compound of Formula I may have the same or different $R^2$ groups on the two pyridyl rings and these may be attached at the same or different ring positions. However, it is especially preferred that substitution be at the 5- and 6-positions, most especially the 6-position, i.e. para to the hydroxyl group. Compound in which the $R^2$ groups are identical and identically located, e.g. 6,6', are especially preferred.

Preferred as groups $R^6$ are mono- or poly(hydroxy or alkoxylated) alkyl groups or a group of the formula $OP(O)(OR^8)R^7$.

$R^7$ is preferably hydroxyl or an unsubstituted alkyl or aminoalkyl group.

Particularly preferred identities for group $R^2$ include $CHR^7OCO(CH_2)_xPh$ and $CHR^7OCO(CH_2CO)_xPh$ (wherein x is 1 to 3), $CHR^7OCOBu^t$, $CH_2N(H)R^{6'}$, $CH_2N(H)R^{6'}$, $N(R^{6'})_2$, $CH_2OH$, $CH_2OR^{6'}$, $COOR^{6'}$, $CON(H)R^{6'}$, $CON(R^{6'})_2$ or $OR^{6'}$ (where $R^{6'}$ is a mono- or polyhydroxylated, preferably $C_{1-4}$, especially preferably $C_{1-3}$, alkyl group), $(CH_2)_nCOOR^{7'}$ (wherein n is 1 to 6), $COOR^{7'}$ (where $R^{7'}$ is a $C_{1-4}$ alkyl, preferably $C_{1-3}$, especially preferably a methyl group), $CH_2OSO_3^-M$, $CH_2CH_2COOH$, $CH_2OP(O)(OH)(CH_2)_3NH_2$, $CH_2OP(O)(OH)CH_3$ or $CH_2OP(O)(OH)_2$ group. Yet more preferably, $R^2$ represents a group of the formula $CH_2OP(O)(OH)_2$.

Compounds of Formula I in which $R^3$ is ethylene and $R^2$ has any of the identities listed above are particularly preferred.

The pharmaceutical composition of the present invention and the preparations included in the kit of the present invention may be formulated with conventional pharmaceutical or veterinary formulation aids, for example stabilizers, antioxidants, osmolality adjusting agents, buffers, pH adjusting agents etc. and may be in a form suitable for parenteral or enteral, administration, for example injection or infusion. Thus the pharmaceutical composition of the present invention may be in a conventional pharmaceutical administration form such as a tablet, capsule, powder, solution, suspension, dispersion, syrup, suppository, etc.

The compounds of Formula I and the metal chelates comprising the compounds of Formula I may therefore be formulated for administration using physiologically acceptable carriers and/or excipients in a manner well-known to those skilled in the art. The compounds of Formula I and the metal chelates comprising the compounds of Formula I may for example be suspended or dissolved in an aqueous medium, optionally with the addition of pharmaceutically acceptable excipients.

The medicament and the pharmaceutical composition according to the present invention may be administered by various routes, for example orally, transdermally, rectally, intrathecally, topically or by means of inhalation or injection, in particular subcutaneous, intramuscular, intraperitoneal or intravascular injection. Other routes of administration may be envisioned if they increase the effectiveness, the bioavailability or the tolerance of the products. The most appropriate route can be chosen by those skilled in the art according to the formulation used.

The cancer inhibiting amount of a medicament administered to a patient is dependent on several different factors such as the type of cancer, the age and weight of the patient, etc., and the attending physician will follow the treatment to adjust the doses if necessary based on laboratory tests.

Generally doses of the active compounds, i.e., first and second compound, in the pharmaceutical composition according to the invention will comprise between 0.01 µmol of the compounds per kilogram of the patient's body weight to 100 µmol of the compound per kilogram of the patient's body weight.

The pharmaceutical composition of the invention may thus comprise a compound of Formula I, in particular DPDP or its dephosphorylated counterparts DPMP and PLED, representing a method for treating various cancer diseases, alone or in combination with other cytostatic drugs or radiotherapy.

If not all of the labile hydrogens of the chelates according to the invention are substituted by the complexed metal ion, biotolerability and/or solubility of the chelates may be increased by substituting the remaining labile hydrogen atoms with physiologically biocompatible cations of inorganic and/or organic bases or amino acids. Examples of suitable inorganic cations include $Li^+$, $K^+$, $Na^+$ and especially $Ca^{2+}$. Suitable organic cations include ammonium, substituted ammonium, ethanolamine, diethanolamine, morpholine, glucamine, N,N,-dimethyl glucamine, lysine, arginine or ornithine.

Where the first or the second compound according to the invention carries an overall charge it may conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The therapeutic agents of the present invention may be formulated with conventional pharmaceutical or veterinary formulation aids, for example stabilizers, antioxidants, osmolality adjusting agents, sweetening agents etc.

As previously described the invention provides a compound of Formula I as defined above for use in the treatment of cancer. When the present inventors compared MnDPDP and DPDP they surprisingly found that DPDP was more efficacious than MnDPDP in its ability to kill cancer cells and they concluded that the previously described cancer cell killing ability of MnDPDP is an inherent property of DPDP. The invention thus provides a new compound for use in treatment of cancer while avoiding the problem of toxicity related to manganese release.

The compound may, as previously mentioned, also be used in combination with a second compound having cyto-protective ability. In an embodiment of the invention is described the use of a metal chelate comprising the compound of Formula I as the compound having the cyto-protective ability. This metal chelate is surprisingly found to be much more stable than MnDPDP and the problem of metal release is thereby avoided. A suitable drug combination for cancer-treatment is thus presented.

The stability of MnDPDP after administration into man is according to prior art mainly governed by the stability constants between DPDP and $Mn^{2+}$ and other competing metals, mainly non-redox active $Zn^{2+}$ which has higher affinity for DPDP than $Mn^{2+}$ (Rocklage et al., Inorg Chem 1989; 28:477-485 and Toft et al., Acta Radiol 1997; 38:677-689). After intravenous injection in man, in addition to dissociation of $Mn^{2+}$, the two phosphates are hydrolyzed from DPDP, giving rise to PLED. Shortly after intravenous injection about 30% of the injected MnDPDP is transformed into MnPLED, and according to prior art (Toft et al., 1997) $Mn^{2+}$ will also dissociate from PLED, actually more readily than from DPDP. Such behaviour of MnPLED is highly supported by the reported stability constants in the literature (Rocklage et al., 1989).

However, reinterpretation of previously published results may in fact suggest that MnPLED is much more stable than MnDPDP (regarding metal stability) during in vivo conditions. If human plasma concentration data taken from the study by Toft et al. 1997 is recalculated it is seen that disappearance of MnDPDP and its 5 metabolites from the plasma roughly parallels that of MnPLED between 30 and 60 minutes (after the initial distribution phase). All these compounds are eliminated from the body through renal excretion, and if manganese dissociated from MnPLED one would expect that these two processes diverged during that period of time. This finding may suggest that MnPLED is stable during in vivo conditions.

Taking the reported stability constants for $Mn^{2+}$ and $Fe^{3+}$ in consideration, the results in Example 3 quite clearly further supports the paradoxical suggestion that MnPLED is much more stable than MnDPDP when it comes to dissociation of $Mn^{2+}$. It may furthermore be anticipated from the pharmacokinetic data that target cells and tissues will not be exposed for concentrations higher than 5 μM of MnPLED, i.e., concentrations where MnPLED are expected to be stable.

The present invention shows that MnPLED is much more stable than MnDPDP, and most importantly, by using MnPLED instead of its mother substance MnDPDP, it may be possible to circumvent the serious toxicological manganese problem evident at frequent therapeutic use in man.

It should furthermore be stressed that pretreatment with MnPLED in mice has shown to be approximately 100 times more efficacious than MnDPDP (EP0910360 and U.S. Pat. No. 6,147,094). This suggests that the MnPLED dose could be considerable lowered in comparison to MnDPDP, which would further reduce the toxicological potential of the pharmaceutical composition, and hence increase the therapeutic index further. Moreover, a lower dose of MnPLED (3 μmol/kg) than that employed in MnDPDP-enhanced diagnostic imaging (5-10 μmol/kg) has been shown to reduce infarct size in pigs (Karlsson et al., Acta Radiol) 2001; 42:540-547), and even much lower doses have been demonstrated to be effective in the same animal model (unpublished data).

Interestingly, MnDPDP did not reduce the infarct size in pigs. This is presumably due to a much faster replacement of manganese for zinc in pigs compared to man. Ten minutes after injection of MnDPDP all manganese has been replaced with zinc (Karlsson et al., 2001), which differs from man (and some other investigated species) where about 30% of the injected manganese stays bound to the chelator for a considerable amount of time. As mentioned previously, the protection of normal cells, in this case myocardial cells, is dependent on redox-active manganese. According to prior art (Rocklage et al., 1989), the stability constant between $Mn^{2+}$ and DPDP is 15.10 (logK), whereas the stability constant between $Zn^{2+}$ and DPDP is 18.95, i.e., $Mn^{2+}$ dissociates about 1000 times more readily than $Zn^{2+}$ from DPDP. The corresponding stability constants between $Mn^{2+}$ and PLED and $Zn^{2+}$ and PLED are 12.56 and 16.68, respectively, i.e., $Mn^{2+}$ once again dissociates about 1000 times more readily than $Zn^{2+}$. From this and the published metabolic scheme (loft et al., 1997) one would not expect any major difference in stability between MnDPDP and MnPLED, in respect to exchange of manganese for zinc, after administration into pigs. The above mentioned infarct reduction seen after administration of MnPLED, but not after MnDPDP, is hence a paradoxical finding. However, the present invention as exemplified in Patent Example 3 comes up with a reasonable explanation to the paradox, namely that MnPLED is a more stable complex than MnDPDP, and most importantly it solves the toxicological problems of manganese instability.

An advantage of combining the DPDP's anticancer activity with MnPLED's cyto-protective activity with regard to normal cells and tissue may be exemplified by the problem of using dexrazoxane as a cardioprotecive agent against anthracycline-induced cardiotoxicity. Although far from evident, dexrazoxane is not recommended at the beginning of the anthracycline therapy in patients with metastatic breast cancer because of the possibility of reducing the anticancer effect of the anthracyclines (Yeh et al., Circulation 2004; 109:3122-3132). However, as has been demonstrated for MnDPDP by the present inventors and others, preclinical data quite clearly shows that this is not a problem when it comes to our approach. One conceivable explanation to this is the two distinct and inherent activities of MnDPDP, namely its anticancer activity and its cytoprotective activity, and which in our invention has been further separated into two distinct chemical entities, namely DPDP, possessing the anticancer activity, and MnPLED, possessing the cytoprotective activity in normal cells and tissues.

BRIEF DESCRIPTION OF THE DRAWINGS

(A) Controls were run in parallel and at the end of the experiments (mean±SD; n=3).

(B) The controls also included absence of iron (—Fe), presence of the iron chelator desferrioxamine (15 μM DFO) or the hydroxyl radical scavenger DMSO (10% DMSO) (mean±SD; n=3).

EXAMPLES

The invention will now be further demonstrated and described by the following non-limiting examples. The examples should be understood to only exemplify the invention and the invention should not be limited thereto.

Example 1

The cytostatic activity of DPDP and MnDPDP was compared by co-incubating human colon cancer cells (SW480) and murine lymphoma cells (J774) with MnDPDP, DPDP and/or oxaliplatin.

Method

The viability of cells was measured using the MTT assay. Briefly, 20,000 SW480 or J774 cells were seeded per well on a 96-well plate and grown over night in Dulbecco's Modified Eagle's Medium (DMEM) containing 10% fetal bovine serum, 2 mM L-glutamine, 100 Ul/ml penicillin and 100 μg/ml streptomycin at 37° C. in humidified air with 5% $CO_2$. Cells were then exposed for 24 h to 50 μM MnDPDP, 50 μM DPDP or 10 μM oxaliplatin at 37° C. The effect of combining 50 μM DPDP with 10 μM oxaliplatin on viability was also tested. The viability of the cells was then assessed by adding 5 mg/ml methylthiazoletetrazolium (MTT) to a final concentration of 0.5 mg/ml and incubating cells for a further 4 h at 37° C. The blue formazan that is formed by mitochondrial dehydrogenases of viable cells was then dissolved over night at 37° C. by adding 10% SDS and 10 mM HCl to a final concentration of 5% SDS and 5 mM HCl. Finally, the absorbance of the solution was read at 570 nm with a reference at 670 nm in a microplate reader Spectramax 340 (Molecular Devices, Sunnyvale, Calif., USA) connected to an Apple Macintosh computer running the program Softmax Pro V1.2.0 (Molecular Devices, Sunnyvale, Calif., USA).

Results

Figure 1:
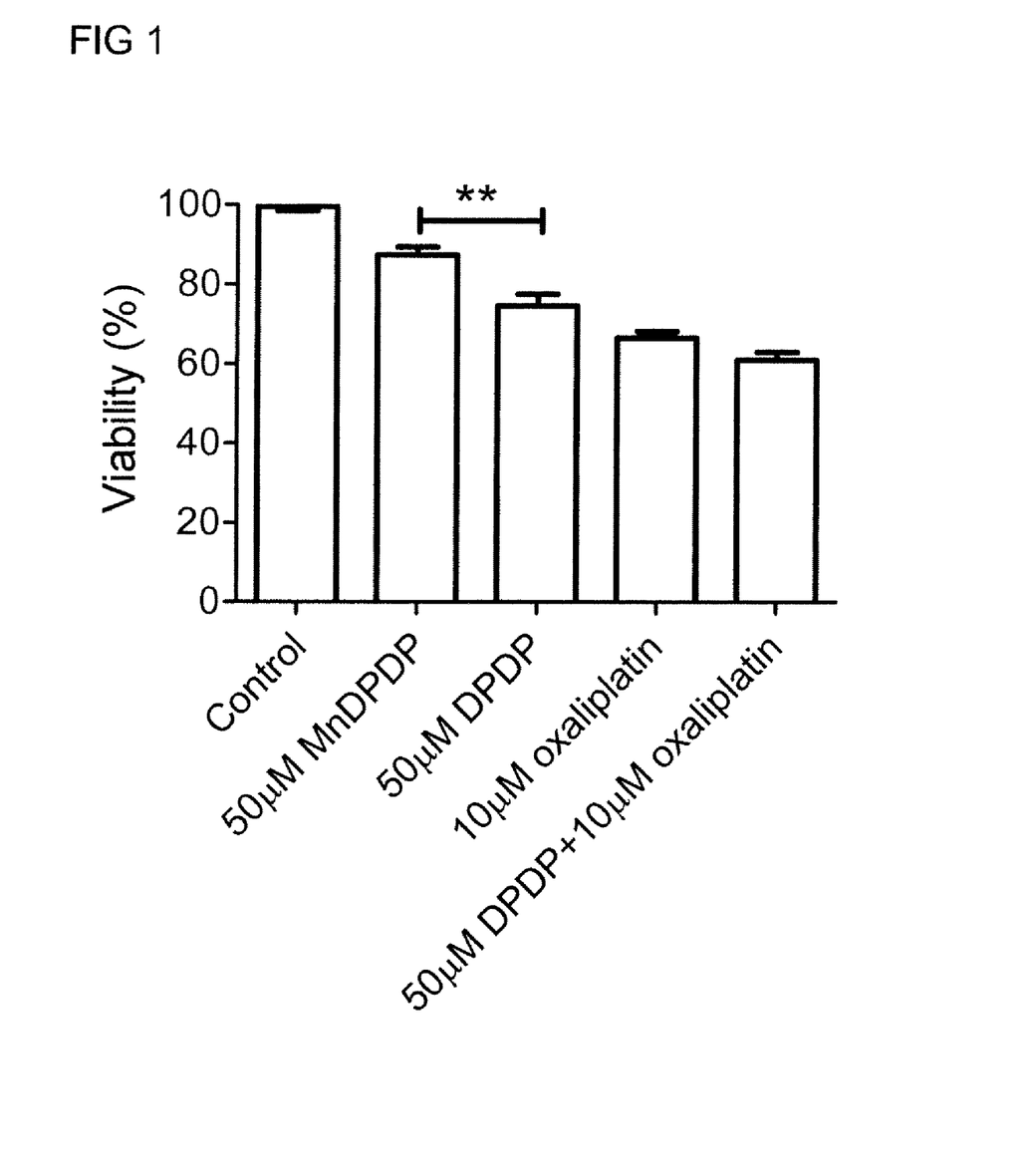
FIG. 1. MTT assay on human colon cancer SW480 cells in absence (control) and presence of MnDPDP, DPDP, oxaliplatin or DPDP+oxaliplatin (mean±SD; n=3).
Figure 2:
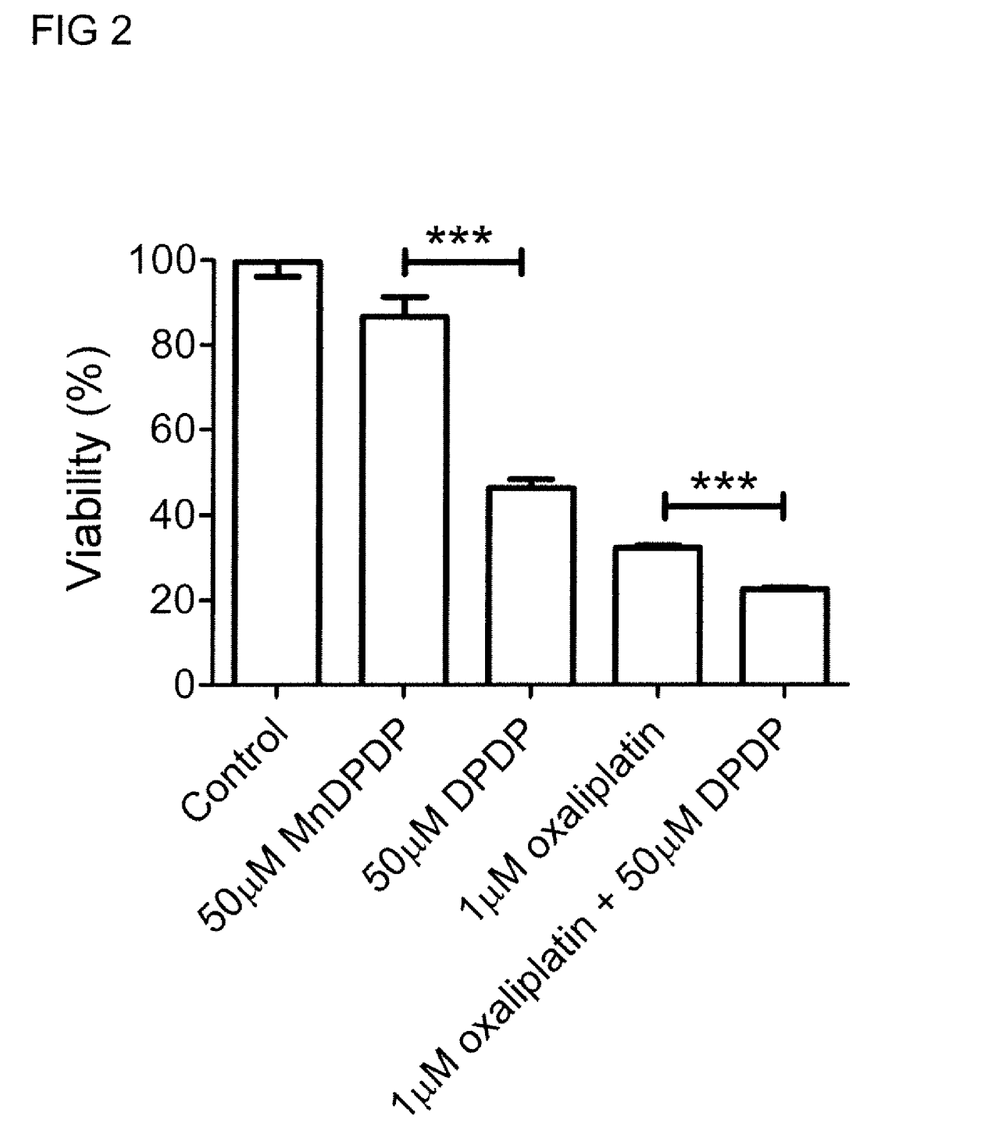
FIG. 2. MTT assay on murine lymphoma J774 cells in absence (control) and presence of MnDPDP, DPDP, oxaliplatin or DPDP+oxaliplatin (mean±SD; n=3).

The cytostatic activity of 50 μM DPDP was statistically significant more efficacious than that of 50 μM MnDPDP in human colon SW480 cells (unpaired t-test) (FIG. 1). There was a tendency, although not statistically significant (p<0.07), that DPDP in combination with oxaliplatin was more potent than oxaliplatin alone in SW480 cells. The corresponding cytostatic activity of 50 μM MnDPDP and 50 μM DPDP in murine lymphoma J774 cells is presented in FIG. 2, and as obvious from this figure, DPDP was significantly more efficacious to kill the lymphoma cells than MnDPDP. Furthermore, DPDP in combination with oxaliplatin was significantly more efficacious than oxaliplatin alone.

Conclusion

When MnDPDP and DPDP were compared it was surprisingly found that DPDP was more efficacious than MnDPDP in its ability to kill cancer cells, and it is concluded that the previously described cancer cell killing ability of MnDPDP is an inherent property of the DPDP.

Example 2

The cytostatic activity of MnDPDP or DPDP in the absence and presence of oxaliplatin was tested in human adenocarcinoma cells (SW620), human ileocecal colorectal adenocarcinoma cells and normal retinal epithelia telomerase immortalized cells (hTERT-RPE1).

Method

HCT-8 cells were grown in RPMI 1640 medium with sodium pyruvate (1 mM) and 10% horse serum. SW620 were grown in ATCC-formulated Leibovitz's L-15 Medium with 10% fetal bovine serum. Cells were kept at 37° C. in a humidified atmosphere containing 5% carbon dioxide. The cells were harvested in the log-phase for experimental use. The fluorometric microculture cytotoxicity assay (FMCA) was used to investigate the cytostatic activity of oxaliplatin, MnDPDP or DPDP and combinations thereof. FMCA is based on measurement of fluorescence generated from hydrolysis of fluorescein diacetate (FDA) to fluorescein by cells with intact plasma membranes. Briefly, 96-well microtiter plates were freshly prepared with drug solutions in triplicates at 10 times the desired drug concentrations. Cell suspensions were seeded into the drug-prepared plates with 20 000 cells per well and plates were then incubated for 72 h. After incubation, the plates were washed, FDA was added, and after 50 min of incubation the fluorescence generated (excitation 480 nm) was measured at 538 nm in a fluorometer (Fluorostar Optima, BMG Technologies). The fluorescence is proportional to the number of cells with intact plasma membrane present in the well.

Results

Figure 3:
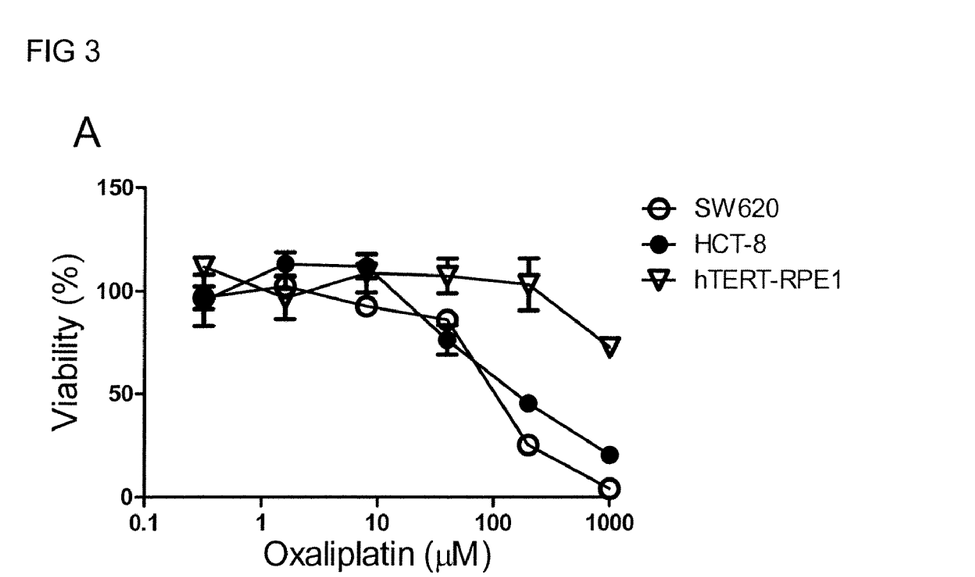
FIG. 3. The cytostatic effect of increasing concentration of oxaliplatin in SW620, HCT-8 and hTERT-RPE1 cells (A). The cytostatic effect of a low concentration oxaliplatin alone or in combination with MnDPDP or DPDP in SW620 (B), HCT-8 (C) hTERT-RPE1 (D) cells (mean±SD; n=3).

The cytostatic activity of increasing concentrations of oxaliplatin in cancer cells (SW620 and HCT-8) and normal cells (hTERT-RPE1) is presented in FIG. 3A. Oxaliplatin demonstrated a concentrations-dependent cytostatic effect in both cancer cell lines but only a slight effect at its highest concentration in normal cells. Neither MnDPDP nor DPDP demonstrated any cytostatic effect in any of these cells (not shown). However, 100 μM DPDP but not MnDPDP significantly (unpaired t-test) potentiated the cytostatic effects of a low concentration (8 μM) of oxaliplatin in both cancer cell lines but not in normal cells (FIG. 3B-D).

Conclusion

When MnDPDP and DPDP were compared it was surprisingly found that DPDP was much more efficacious than MnDPDP in its ability to increase the cancer-killing ability of oxaliplatin, and it is concluded that the previously described cancer cell killing ability of MnDPDP is an inherent property of the DPDP.

Example 3

By permitting the chelator DPDP, the metal complexes MnDPDP and MnPLED to compete with iron in the Fenton assay, the stability of MnDPDP and MnPLED was compared.

Method

Ferric iron (10 µM) was partially reduced to its ferrous form by cysteine (100 µM) in 150 mM acetate buffer. $H_2O_2$ (100 µM) was added to initiate the production of hydroxyl radicals (HO.). The latter oxidize $H_2DCF$ (non-fluorescent 2',7'-dichlorodihydrofluorescein; 5 µM) to fluorescent DCF (2',7'-dichlorofluorescein). $H_2DCF$ was obtained by hydrolysing its acetate ester ($H_2DCF$-DA)]. DMSO (10%) and DFO (10 µM) were used to demonstrate the formation of HO. and the involvement of iron respectively. DPDP, MnDPDP and MnPLED at various concentrations were assayed for their iron-chelating capacity. Fluorescence was measured in an FL600 Microplate Fluorescence reader (Bio-Tek, Winooski, Vt., U.S.A.) at ex 485 nm and em 530 nm.

Results

Figure 4:
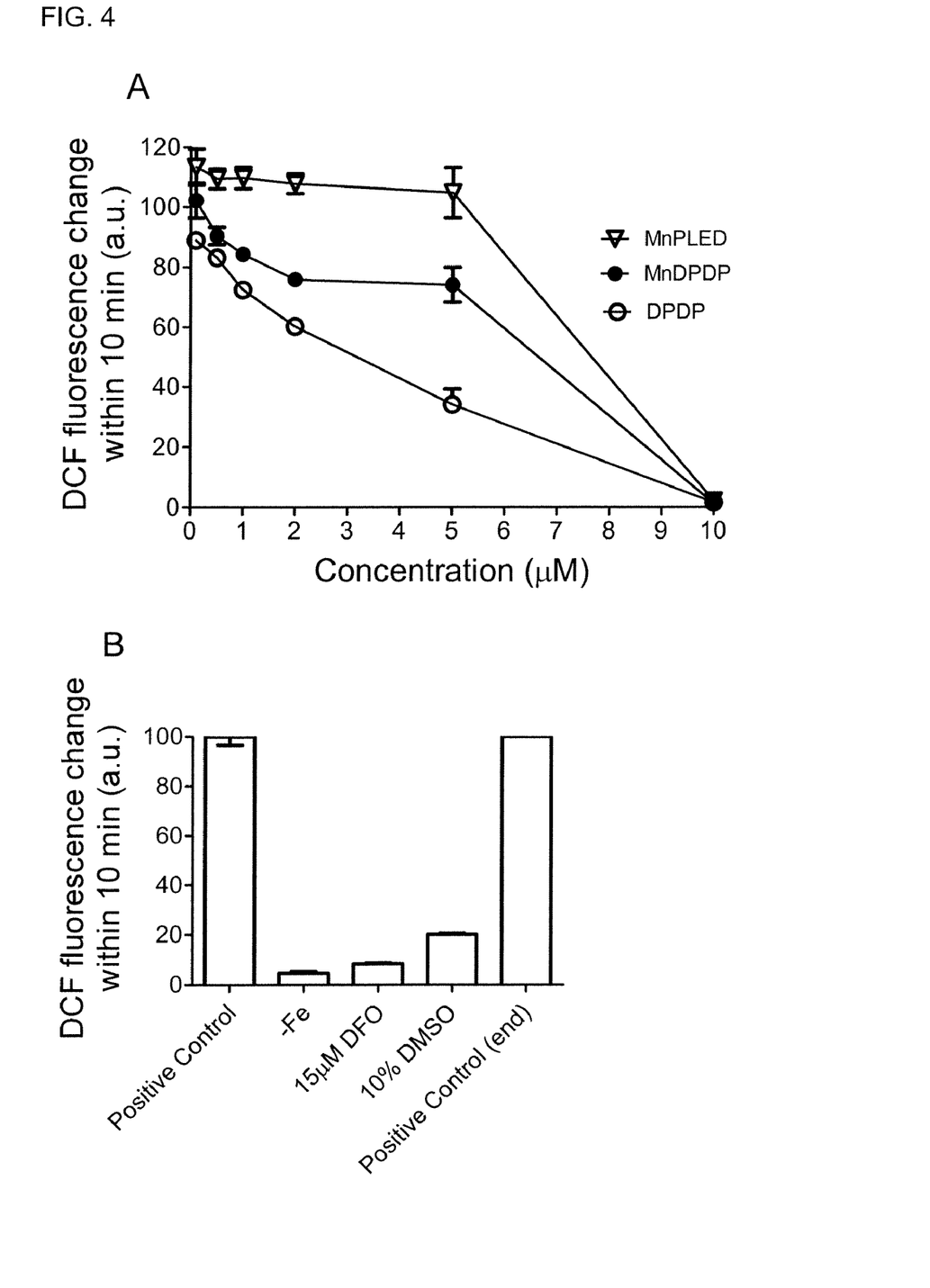
FIG. 4. The Fenton assay in the presence of various concentrations DPDP, MnDPDP and MnPLED (mean±SD; n=3).

FIG. 4 demonstrates that DPDP inhibited the Fenton reaction in a dose-dependent manner; the inhibition started at 0.1 µM and was completed at 10 µM. The inhibitory pattern is in accordance with the reported high affinity of DPDP for ferric iron (log K=33.52). However, in the case of MnPLED no inhibition was evident up to and including a concentration of 5 µM but at 10 µM the inhibition was complete. The iron-chelating capacity of MnDPDP was significantly higher than that of MnPLED.

Conclusion

The present results are in opposite to and highly surprising to what one would expect from both the reported iron- and manganese-chelating capacity of MnDPDP and MnPLED. The reported stability constants between $Fe^{3+}$ and DPDP and between $Fe^{3+}$ and PLED are 33.52 and 36.88 (logK), respectively, whereas the reported stability constants between $Mn^{2+}$ and DPDP and $Mn^{2+}$ and PLED are 15.10 and 12.56, respectively (Rocklage et al., 1989). One would hence expect MnPLED to be a much better inhibitor of the Fenton reaction than MnDPDP.

The invention claimed is:

1. A method for treatment of cancer selected from lymphoma, colorectal cancer and/or metastases thereof, and breast cancer and/or metastases thereof, in a human or non-human body, said method comprising administrating to said body a cancer-inhibiting amount of a first compound of Formula I:

(I)

or a physiologically acceptable salt thereof, wherein
X is CH or N,
each $R^1$ independently is hydrogen or —$CH_2COR^5$;
$R^5$ is hydroxy, optionally hydroxylated alkoxy, amino or alkylamido;
each $R^2$ independently is a group $ZYR^6$;
Z is a bond, or a $C_{1-3}$ alkylene or oxoalkylene group optionally substituted by a group $R^7$;
Y is a bond, an oxygen atom or a group $NR^6$;
$R^6$ is a hydrogen atom, $COOR^8$, an alkyl, alkenyl, cycloalkyl, aryl or aralkyl group optionally substituted by one or more groups selected from $COOR^8$, $CONR^8_2$, $NR^8_2$, $OR^8$, =O, $OP(O)(OR^8)R^7$ and $OSO_3M$;
$R^7$ is hydroxy, an optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation;
$R^3$ is a $C_{1-8}$ alkylene group, a 1,2-cykloalkylene group, or a 1,2-arylene group, optionally substituted with $R^7$; and
each $R^4$ independently is hydrogen or $C_{1-3}$ alkyl.

2. The method of claim 1, wherein:
$R^5$ is hydroxy, $C_{1-8}$ alkoxy, ethylene glycol, glycerol, amino or $C_{1-8}$ alkylamido;
Z is a bond or a group selected from $CH_2$, $(CH_2)_2$, CO, $CH_2CO$, $CH_2CH_2CO$ and $CH_2COCH_2$;
Y is a bond;
$R^6$ is a mono- or poly(hydroxy or alkoxylated) alkyl group or a group of the formula $OP(O)(OR^8)R^7$; and
$R^7$ is hydroxy, or an unsubstituted alkyl or aminoalkyl group.

3. The method of claim 2, wherein $R^3$ is ethylene and each group $R^1$ represents —$CH_2COR^5$ in which $R^5$ is hydroxy.

4. The method of claim 1, wherein the first compound is N,N'-dipyridoxyl ethylenediamine-N,N'-diacetic acid.

5. The method of claim 1, wherein the first compound is N,N'-bis-(pyridoxal-5-phosphate)-ethylenediamine-N,N'-diacetic acid.

6. The method of claim 1, wherein the cancer is colon cancer and/or metastases thereof.

7. The method of claim 1, wherein the cancer is breast cancer and/or metastases thereof.

8. The method of claim 1, wherein the cancer is lymphoma,

9. The method of claim 1, wherein the first compound is administered with a cyto-protective amount of a metal chelate of a compound of Formula I.

10. The method of claim 9, wherein said metal chelate has a $K_a$ value in the range of from $10^8$ to $10^{24}$.

11. The method of claim 9, wherein said metal chelate has a lower $K_a$ value than the $K_a$ value of an iron ($Fe^{3+}$) chelate of a compound of Formula I, by a factor of at least $10^3$.

12. The method of claim 9, wherein the metal chelate is a manganese ($Mn^{2+}$ or $Mn^{3+}$) or copper ($Cu^+$ or $Cu^{2+}$) chelate.

13. The method of claim 9, wherein the first compound is N,N'-dipyridoxyl ethylenediamine-N,N'-diacetic acid and metal chelate is a metal chelate of N,N'-dipyridoxyl ethylenediainine-N,N'-diacetic acid.

14. The method of claim 9, wherein the first compound is N,N'-bis-(pyridoxal-5-phosphate)-ethylenediamine-N,N'-diacetic acid and the metal chelate is a metal chelate of N,N'-dipyridoxyl ethylenediamine-N,N'-diaretic acid.

15. The method of claim 1, wherein the first compound is administered together with one or more other anti-cancer drugs selected from the group consisting of doxorubicin, epirubicin, cisplatin, carboplatin, paclitaxel, 5-fluorouracil, cyclophosphamide, gemcitabine, irinotecan, and methotrexate.

16. The method of claim 15, wherein the first compound and the one or more other anti-cancer drug(s) are administered simultaneously, separately or sequentially to said patient.

17. The method of claim 1, wherein the first compound is administered in combination with radiation therapy.

* * * * *

UNITED STATES PATENT AND TRADEMARK OFFICE
CERTIFICATE OF CORRECTION

PATENT NO. : 8,377,969 B2  
APPLICATION NO. : 12/808144  
DATED : February 19, 2013  
INVENTOR(S) : Jan Olof G. Karlsson, Tino Kurz and Rolf Andersson Page 1 of 1

It is certified that error appears in the above-identified patent and that said Letters Patent is hereby corrected as shown below:

In the Claims:

Claim 1, Column 12, Line 2, after "$OR^8$," insert --=$NR^8$,--.

Claim 15, Column 12, Line 55, insert --oxaliplatin,-- after "epirubicin,".

Signed and Sealed this  
Twenty-eighth Day of May, 2013

Teresa Stanek Rea  
*Acting Director of the United States Patent and Trademark Office*